United States Patent [19]

Zaiger

[11] Plant 4,917

[45] Nov. 2, 1982

[54] PEACH TREE

[76] Inventor: Chris F. Zaiger, 537 Rosemore Ave., Modesto, Calif. 95351

[21] Appl. No.: 255,389

[22] Filed: Apr. 20, 1981

[51] Int. Cl.[3] ..... A01H 5/03

[52] U.S. Cl. ..... Plt./43

[58] Field of Search ..... Plt./43

*Primary Examiner*—Robert E. Bagwill

[57] ABSTRACT

This new and distinct variety of Peach tree which is of large size, vigorous upright growth, being a productive and regular bearer of medium to large, firm, yellow flesh, clingstone fruit having yellow skin substantially overspread with red. The fruit is further characterized by its early maturity, good eating quality, firm flesh and the ability to ship to long distance markets.

1 Drawing Figure

ORIGIN OF THE VARIETY

The present variety of peach tree was developed by me in my experimental orchard located in Modesto, Calif., as a second generation seedling of a cross between Sam Houston Peach (non-patented) and May Grand Nectarine (U.S. Plant Pat. No. 2,794). I maintained the selection under careful and continual observation during which time I recognized its desireable characteristics described above and selected the variety for reproduction.

ASEXUAL REPRODUCTION OF THE VARIETY

The present variety of peach tree was asexually propagated by budding and grafting, as performed by me at Modesto, Calif., shows that said characteristics come true to form and are established and transmitted through succeeding propagations.

SUMMARY OF THE VARIETY

The present variety of peach tree is of large size, vigorous, upright in growth and productive and regular bearer of large size, early ripening, yellow flesh, clingstone fruit. The fruit is further characterized by having a high degree of red skin color, uniform ripening, firm flesh and good eating and shipping quality.

BRIEF DESCRIPTION OF THE PHOTOGRAPH

The accompanying photographs show typical specimens of the fruit and foliage of the new variety, with the upper and lower surfaces of the leaves being illustrated and a fruit divided on its suture plane to reveal flesh coloration and showing a stone remaining in place. The illustrations were taken shortly after being picked at maturity (shipping ripe) and the colors are as nearly true as reasonably possible in a color representation of this type.

DESCRIPTION OF THE VARIETY

The botanical details of this new and distinct variety of peach tree, as based upon observations of specimens grown at Modesto, Calif., with color terminology in accordance with Reinhold Color Atlas by A. Korneruf and J. H. Wanscher.

Tree:
- *Size.*—Medium to large.
- *Vigor.*—Vigorous.
- *Form.*—Upright.

- *Density.*—Medium dense.
- *Shape.*—Normally pruned to vase shape.
- *Production.*—Productive.
- *Bearing.*—Regular.

Trunk:
- *Size.*—Medium to large.
- *Texture.*—Shaggy.

Branches:
- *Size.*—Medium to large.
- *Texture.*—Medium rough.
- *Lenticels.*—Medium size. Medium number.
- *Color.*—Brown to reddish brown.

Leaves:
- *Size.*—Average length — $7\frac{5}{8}''$. Average width — $1\frac{3}{4}''$.
- *Form.*—Lanceolate. Tip Acuminate.
- i Margin.—Crenate.
- *Petiole.*—Average length — 7/16". Average width — 1/16". Longitudinally grooved.
- *Glands.*—Globose. Medium size. Number varies from 1 to 4. Average number 2. Positioned on base of blade and upper part of petiole, usually alternate.
- *Color.*—Upper surface — dark green (27-F-8) to (28-F-7). Lower surface — grayish green (29-D-6) to (29-E-6).

Flower buds:
- *Size.*—Medium size. Medium length.
- *Form.*—Plump.
- *Pubescence.*—Pubescent.

Flowers:
- *Size.*—Large — showy.
- *Bloom period.*—Feb. 24, 1977 to Mar. 5, 1977. Varies slightly with climatic conditions.
- *Pollen.*—Present.
- *Color.*—Pink.

Fruit:
- *Maturity when described.*—Hard ripe.
- *Date of first picking.*—May 27, 1977.
- *Date of last picking.*—June 2, 1977.
- *Size.*—Medium to large. Average diameter axially — $2\frac{1}{2}''$ to $2\frac{3}{4}''$. Average transversely in suture plane — $2\frac{1}{2}''$ to $2\frac{3}{4}''$.
- *Form.*—Globose to slightly flattened at stem end. Nearly symmetrical.
- *Suture.*—Distinct but shallow — extends from base to apex.
- *Ventral surface.*—Usually rounded — varies from equal to unequal.

*Base.*—Retuse.

*Cavity.*—Rounded to slightly elongated in suture plane. Average depth — ½". Average breadth — 1".

*Apex.*—Rounded. Varies from slight point to slight depression.

Skin:

*Thickness.*—Medium.

*Texture.*—Medium.

*Tendency to crack.*—None.

*Down.*—Moderate. Medium length.

*Color.*—Bright yellow ground color yellow to flame yellow (3-A-8) to (4-A-8). Red blush covering most of the surface (8-A-8) to (9-B-8).

Flesh:

*Texture.*—Firm.

*Amygdalin.*—Undetected.

*Juice.*—Moderate.

*Ripens.*—Uniform.

*Flavor.*—Sub-acid to mild.

*Aroma.*—Distinct.

*Eating quality.*—Good.

*Fibers.*—Few and tender.

*Color.*—Orange yellow (4-A-8) to golden yellow (5-A-7).

Stone:

*Type.*—Clingstone.

*Size.*—Medium. Average length — 1 3/16". Average breadth — 1". Average thickness — ¾".

*Form.*—Ovid.

*Base.*—Straight to slightly oblique.

*Apex.*—Acuminate.

*Side.*—Equal to slightly unequal.

*Surface.*—Irregularly furrowed toward apex, pitted toward base.

*Ridges.*—Rounded toward base.

*Tendency to split.*—Very slight.

*Color.*—Light brown — (8-C-4) to (8-D-4).

Use: Dessert.

*Market.*—Local and long distance shipping.

Keeping quality: Good.

Shipping quality: Good.

The peach tree and its fruit herein described, may vary in slight detail due to climatic, soil conditions and cultural practices under which the variety may be grown; the present description being of the variety as grown by me in my experimental orchard at Modesto, Calif.

I claim:

1. A new and distinct variety of peach tree, substantially as illustrated and described, characterized by it's large size, vigorous and upright growth, a productive and regular bearer of medium to large, firm, yellow flesh, clingstone fruit, maturing six days after Royal Gold peach (U.S. Plant Pat. No. 2,663), but having firmer fruit, with heavier production; the fruit is further characterized by its high degree of attractive red skin color, its good eating quality and the high degree of firmness when mature provides for good shipping characteristics.

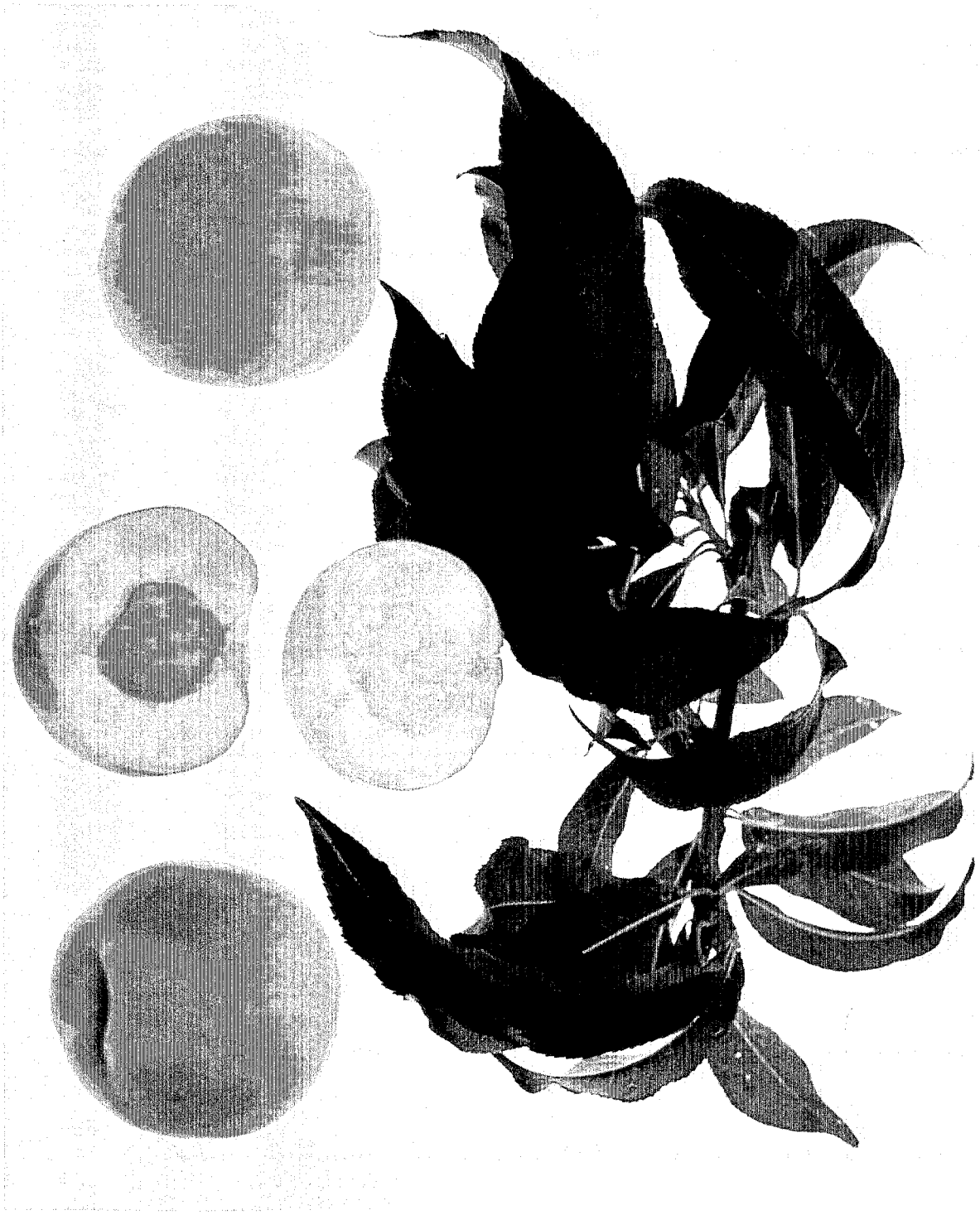

* * * * *